(12) United States Patent
Chandler et al.

(10) Patent No.: US 10,094,755 B1
(45) Date of Patent: Oct. 9, 2018

(54) ENVIRONMENTAL SENSOR AND METHOD OF OPERATING THE SAME

(71) Applicant: Venturedyne, Ltd., Pewaukee, WI (US)

(72) Inventors: David L. Chandler, Highland, CA (US); Glenn Y. Kozuma, Twin Peaks, CA (US)

(73) Assignee: Venturedyne, Ltd, Pewaukee, WI (US)

( * ) Notice: Subject to any disclaimer, the term of this patent is extended or adjusted under 35 U.S.C. 154(b) by 0 days.

(21) Appl. No.: 15/793,758

(22) Filed: Oct. 25, 2017

(51) Int. Cl.
| | |
|---|---|
| *G01N 21/00* | (2006.01) |
| *G01N 15/02* | (2006.01) |
| *G01N 15/12* | (2006.01) |
| *G01N 35/00* | (2006.01) |
| *G01N 21/53* | (2006.01) |
| *G01N 15/14* | (2006.01) |
| *G01N 15/00* | (2006.01) |

(52) U.S. Cl.
CPC ..... *G01N 15/0205* (2013.01); *G01N 15/1227* (2013.01); *G01N 21/53* (2013.01); *G01N 35/00871* (2013.01); *G01N 2015/0046* (2013.01); *G01N 2015/0053* (2013.01); *G01N 2015/1486* (2013.01); *G01N 2015/1493* (2013.01)

(58) Field of Classification Search
CPC .......... G01N 15/0205; G01N 15/1227; G01N 21/53; G01N 35/00871; G01N 2015/0046; G01N 2015/0053; G01N 2015/1486; G01N 2015/1493
USPC .................................................. 356/335–343
See application file for complete search history.

(56) References Cited

U.S. PATENT DOCUMENTS

| | | |
|---|---|---|
| 4,893,928 A | 1/1990 | Knollenberg |
| 4,984,889 A | 1/1991 | Sommer |
| 5,011,286 A | 4/1991 | Petralli |
| 5,084,629 A | 1/1992 | Petralli |
| 5,515,164 A | 5/1996 | Kreikebaum et al. |
| 5,600,438 A | 2/1997 | Kreikebaum et al. |
| RE37,353 E | 9/2001 | Kreikebaum et al. |

*Primary Examiner* — Tri T Ton
(74) *Attorney, Agent, or Firm* — Michael Best & Friedrich LLP (57) ABSTRACT

A gaseous-fluid environmental sensor having a gaseous-fluid flow system. The gaseous-fluid flow system, in one construction, includes a blower to move the gaseous fluid from an intake port to an exhaust port via a flow path. The gaseous-fluid environmental sensor further includes a controller coupled to a particle count sensor. The controller determines whether the particle count sensor has a fault based on the particle count sensor not sensing a particle or a cosmic ray in a time period.

17 Claims, 11 Drawing Sheets

ENVIRONMENTAL SENSOR AND METHOD OF OPERATING THE SAME

BACKGROUND

The invention relates to environmental sensors, such as particle counters that are used to detect particles in air or liquid environments.

Particle counters that detect microscopic particles in air and gases are used to monitor clean environments and process gasses where contamination of a product being manufactured can render that product unsuitable for its intended purpose.

Pharmaceutical manufacturers maintain controlled environments that meet cleanliness standards for the maximum number of particles greater than a certain size occupying a specified volume of air. Environments where pharmaceutical products are formulated and packaged are regulated by government agencies to insure compliance to cleanliness standards.

Semiconductor and aerospace manufacturers also monitor the cleanliness of their process gases and controlled environments in order to eliminate sources of contamination and increase yield. Other industries, for example those that make automotive products, micro-machined structures and optical assemblies also monitor their environments to detect and control contamination that affects product performance and quality.

The sensors used in particle counters to monitor controlled environments include a means of moving a measured and controlled volume of air through the sensor. The sensor consists of a light source, collection optics, photodetector, circuitry for converting detected scattered light to electrical signals, a means of discriminating electrical signals caused by particles at the sizes of interest and a means of counting the number of times that those signals occur over some period of time.

The photodetector and electronic signal processing used in the sensor are optimized for detection of photons that are refracted or reflected by a particle as it intercepts the beam of light. The photodetector, typically a PIN photo diode converts the photons to a current that produces a voltage that is a function of particle size.

Cosmic rays, which include gamma rays and x-rays, are forms of radiation that can also cause a pulse of current to occur when they intercept the photodetector. Photodetectors are unable to distinguish between these forms of radiation and the burst of photons that result from a particle intercepting the light beam. Because these pulses occur in the absence of light, they are commonly referred to as "dark pulses" and the pulses produce "dark counts". Dark counts are a nuisance to particle counting systems since they can cause errors in the particle count the system reports.

Accordingly, there is the need for a new and useful environmental sensor with an improved technique to address dark counts.

SUMMARY

In one embodiment, the invention provides a gaseous-fluid environmental sensor. The environmental sensor includes a gaseous-fluid flow system defining a flow path for a fluid, a particle count sensor to sense particles in the fluid and a cosmic ray, and a controller electrically coupled to the particle count sensor. The controller is further configured to store a dark count, store a compensated particle count based on the signal from the particle count sensor and the dark count, and determine whether the particle count sensor has a fault based on the particle count sensor not sensing a particle or a cosmic ray in a time period.

In another embodiment, the invention provides a method of controlling a gaseous-fluid environmental sensor having a particle count sensor. The method includes creating a flow of fluid from a space through the gaseous-fluid environmental sensor; sensing particles in the fluid with the particle count sensor; sensing cosmic rays with the particle count sensor; storing a dark count; storing a compensated particle count based on the sensed particles, the sensed cosmic rays, and the stored dark count; and determining whether the particle count sensor has a fault based on the particle count sensor not sensing a particle or a cosmic ray in a time period.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

Although directional references, such as upper, lower, downward, upward, rearward, bottom, front, rear, etc., may be made herein in describing the drawings, these references are made relative to the drawings (as normally viewed) for convenience. These directions are not intended to be taken literally. In addition, terms such as "first", "second", and "third" are used herein for purposes of description and are not intended to indicate or imply relative importance or significance.

Dark counts are a nuisance to particle counting systems since they can cause errors in the particle count the system reports. Various methods are employed to minimize these errors.

1. Dark count detector: A detector may be included in the system for the purpose of detecting dark pulses. This detector only produces dark counts. These counts are subtracted from the counts produced by the particle detector that includes both particle counts and dark counts. The dark counts are subtracted at a rate that coincides with the frequency of dark counts that the system is detecting.

2. Coincidence detector: Two detectors may be configured to detect light and produce a pulse from the same particle as it passes through the beam. A circuit can detect if both detectors are producing a pulse simultaneously and if so, count it as a particle. The probability of two dark pulses happening on two separate detectors coincidentally is low enough to be ignored.

3. Detector array: Use of a detector array and a signal processing system that ignores a signal from a single array element that could be caused by a cosmic ray and qualifies a particle by requiring signals simultaneously on multiple elements of the array. The individual elements of the array have a small area which makes them less susceptible to cosmic rays and the combined elements of the array combine to detect light over a large area suitable for the optical collection system.

4. Estimated dark count subtraction: Subtraction of particle counts at a rate that coincides with the average rate of dark counts anticipated to be detected by the system. This method may over subtract or under subtract depending on the frequency of actual dark counts compared to the counts anticipated. The rate of dark count subtraction is determined so that count errors are negligible.

The particle counting system subject to this disclosure has a detection system and a counting system. The photodetector and analog signal processing system used in a particle counter detection system can fail in a mode where the signal presented to the counting system has no particle pulses or dark pulses.

In this case, the zero counts presented by the system will be favorable to a user for whom high counts are a cause for investigation. For such users, counts of zero are good and in some cases can go unquestioned for a shift or a day or even longer. If the counter is found to have been giving false data and not reporting possible alarm conditions, a deviation investigation may be required to determine the liability and risk and determine what corrective action should be taken. The corrective action could be a decision to quarantine and possibly scrap the product that was being produced.

Figure 1:
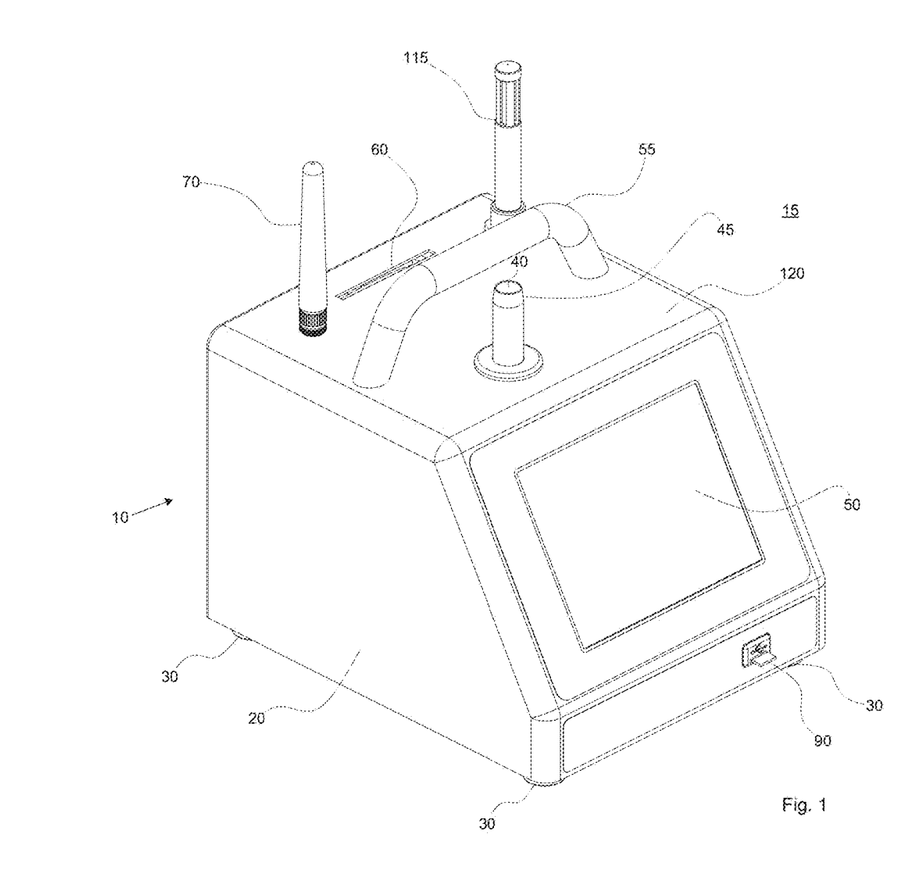
FIG. 1 is a perspective view of a portable gaseous-fluid particle counter from a first vantage point.
Figure 2:
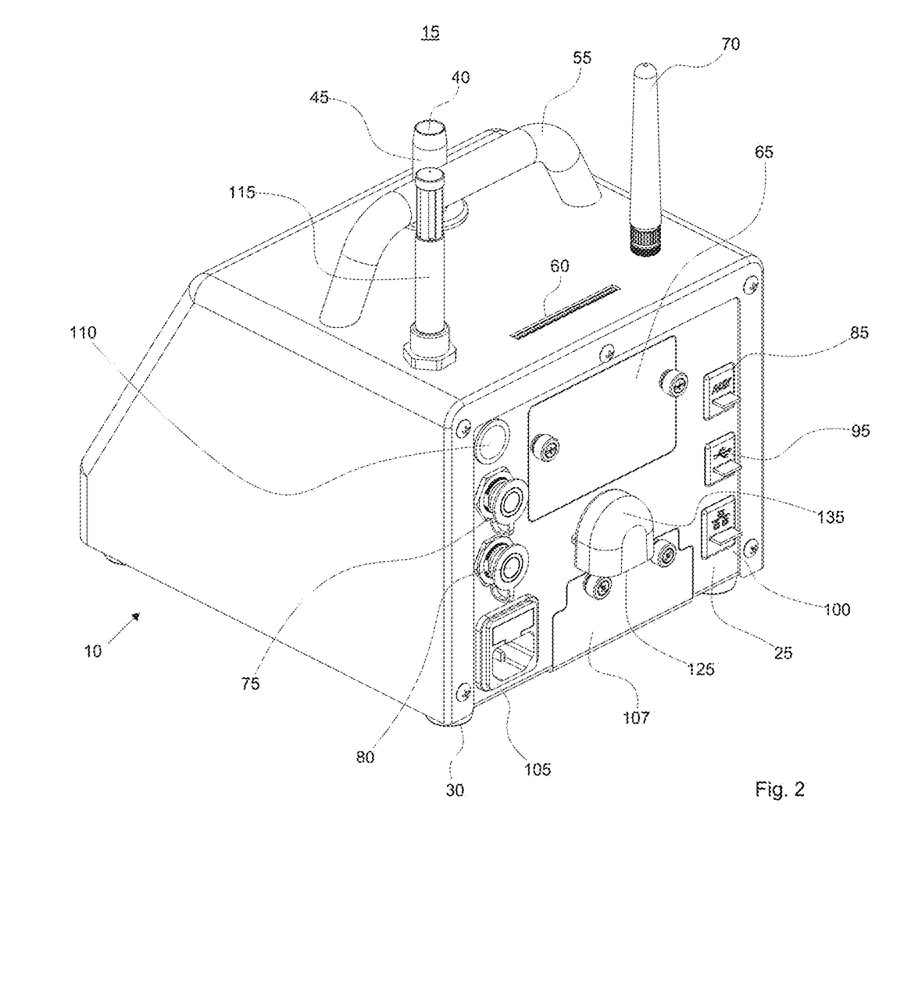
FIG. 2 is a perspective view of the particle counter of FIG. 1 from a second vantage point.

FIGS. 1 and 2 illustrate an exemplary environmental sensor. The environmental sensor is a portable gaseous-fluid particle counter 10 for counting and collecting microbial particles from a gaseous fluid of an environment 15. It is to be understood that microbial particles can include biologically active particles such as bacteria, fungi, and similar particles. Moreover, the term gaseous fluid makes reference to ambient air and other gaseous fluid that may not be considered as ambient air, such as, but not limited to, air in a clean room environment. The shown exemplary environmental sensor of FIGS. 1 and 2 was disclosed in U.S. patent application Ser. No. 14/972,829, filed on Dec. 17, 2015, the content of which is incorporated herein by reference. While the particle counter 10 is shown throughout the figures, aspects of the invention can be used in other environmental sensors, which may also encompass environmental filters. The particle counter 10 shown in the figures is an exemplary construction and it is to be understood that other physical appearances fall within the scope of the invention.

FIGS. 1 and 2 illustrate an exemplary environmental sensor. The environmental sensor is a portable gaseous-fluid particle counter 10 for counting and collecting microbial particles from a gaseous fluid of an environment 15. It is to be understood that microbial particles can include biologically active particles such as bacteria, fungi, and similar particles. Moreover, the term gaseous fluid makes reference to ambient air and other gaseous fluid that may not be considered as ambient air, such as, but not limited to, air in a clean room environment. The shown exemplary environmental sensor of FIGS. 1 and 2 was disclosed in U.S. patent application Ser. No. 14/972,829, filed on Dec. 17, 2015, the content of which is incorporated herein by reference. While the particle counter 10 is shown throughout the figures, aspects of the invention can be used in other environmental sensors, which count particles in a clean gaseous fluid where low counts approaching zero are a desirable measurement. The particle counter 10 shown in the figures is an exemplary construction and it is to be understood that other physical appearances fall within the scope of the invention. For example a particle counter could operate without a display or printer and have a data connection to a computer that provides functions for data collection and reporting. Another example is a particle counter having a sensor that is connected to a vacuum pump that is external to the particle counter and located outside of the clean environment. It this case, the particle counter would not necessarily include a display, printer or pump.

With reference to FIGS. 1-2, the particle counter 10 includes a support structure, such as a housing, which may be divided into a top enclosure 20 and a bottom enclosure 25. However, the support structure does not need to be solely the housing. Rather, the support structure can include additional structure for supporting the gaseous-fluid flow system (discussed below), which is then enclosed by the housing. The particle counter 10 also includes a set of supports 30. The supports 30 help the particle counter 10 sit in a first orientation, which is shown in FIGS. 1-2, defining a gaseous fluid intake port 40 facing upward. The just-described orientation is relative to the position of the particle counter 10 within the FIGS. 1 and 2. It is to be understood that the intake port 40 may be at other orientations.

The gaseous fluid intake port 40 is formed by an inlet structure, which is shown as an inlet tube 45. However, other environmental sensors and particle counters may use other inlet structures to receive a fluid depending on the type of fluid being acquired. Other inlet structures are shown in, for example, the above referenced patents.

The particle counter 10 also includes a user interface for a user to operate the particle counter 10 and/or to view information related to the particle counter 10 and the samples collected by the particle counter 10. The user interface is shown as a display 50 and a power/reset button 110. The user can view information provided by the particle counter 10 via the display and control the operation of the particle counter 10 via the power/reset button 110. Other constructions of the particle counter 10 can include different types of user interfaces, such as touch displays, liquid crystal displays, light emitting diodes, incandescent lights, keypads or keyboards, buttons, switches, pointing devices, touch pads, etc.

In the construction shown, the particle counter 10 includes a handle 55 mounted to the top enclosure 20. The handle 55 allows a user to transport the particle counter 10 between different locations; i.e., the shown particle counter 10 is portable. Also shown are a printer slot 60 and a printer door 65. A printer is housed in the particle counter 10, receives paper by way of the printer door 65, and dispenses printed paper through the printer slot 60.

The particle counter 10 can wirelessly communicate with one or more remote devices via a wireless antenna 70 or can communicate via wired connections. Exemplary wired connections shown include input/output connectors 75 and 80, an RJ-11 auxiliary connector 85, a USB type A connector 90, a USB type B connector 95, and an Ethernet connector 100. While various connector types and protocol types are mentioned, these types are only exemplary.

The particle counter 10 shown also includes a port 105 to receive a power cord, a battery door 107, a power/reset button 110, and a room humidity and temperature sensor 115.

The intake port 40 shown in FIGS. 1-2 is located on a top panel 120 of the top enclosure 20. An exhaust port 125 of an outlet structure exhausts gaseous fluid external to the particle counter 10. The exhaust port 125 is shown in FIG. 2 as being on a side panel 130 of the bottom enclosure 25 and the outlet structure includes an outlet tube 135 in the shape of a shroud for deflecting the gaseous fluid.

With reference to FIGS. 3 through 7, the particle counter 10 includes a support platform 140 for supporting the internal components (e.g., a control system and a gaseous-fluid flow system) of the particle counter 10. The gaseous-fluid flow system includes the inlet structure (i.e., the inlet tube 45), a particle count sensor 145, a flow connect block 150, a sensor/blower mounting plate 155, a blower 160, a filter 165, a flow shunt 170, a flow sensor 175, the outlet structure (e.g., the outlet tube 135), and conduit (discussed below). The gaseous-fluid flow system is shown in FIGS. 3 through 6 as having a particular order. However, the order of the elements may change with different constructions. For a simple example, the filter 165 may be placed after the flow shunt 170. Other arrangements will be discussed below, but all the different permutations will not be discussed herein. The control system includes a DC power source (e.g., a battery) 180, a power supply 185, a motor sensor 190, the particle count sensor 145, the flow sensor 175, a controller 195, drive circuit 200, motor 205, and communication input/output interface 210. The control system can include other control elements not shown in FIG. 7, such as the user interface (e.g., display 50), other sensors (e.g., room humidity/temperature sensor 115), and the printer.

Referring again to FIGS. 3 through 7, the blower 160 is driven by a motor 205 to move gaseous-fluid through the particle counter 10. The blower is fluidly connected to the intake port 40 and is also fluidly connected to the exhaust port 125. The blower draws gaseous fluid from the environment 15 into the intake port 40 and through the particle count sensor 145 for counting particles. From the particle count sensor 145, the blower 160 continues to draw the gaseous fluid through the flow connect block 150 and the sensor/blower mounting plate 155, and into the blower 160. The blower 160 then pushes the gaseous fluid to the filter 165. Particles in the gaseous fluid are filtered by the filter 165 depending on the type of filter used. After being pushed through the filter 165, the gaseous fluid enters the flow shunt 170. The flow shunt 170 includes a fluid restrictor 215 (best shown in FIG. 4) that shunts a small amount of gaseous fluid for flow sensing. A conduit 220 provides a channel for the shunted fluid toward the flow sensor 175. The flow sensor 175 senses a parameter relating to the flow of the gaseous fluid through the flow path based on the shunted fluid. The shunted fluid returns to the flow shunt 170 via conduit 225. The returned gaseous fluid recombines with the main gaseous fluid flow and exhausts from the exhaust port 125.

The particle count sensor 145 is configured to detect particles within a predetermined size range. The shown particle count sensor 145, in one construction, is an aerosol particle counter that operates under the principle of light scattering detection. However, other aerosol particle counters (e.g., a particle counter that operates under the principle of light obscuration) and other particle counters can be used depending on the type of environment. The flow enters the particle count sensor 145 through a sensor intake port 230 and exits through a sensor exhaust port 235.

Figure 8:
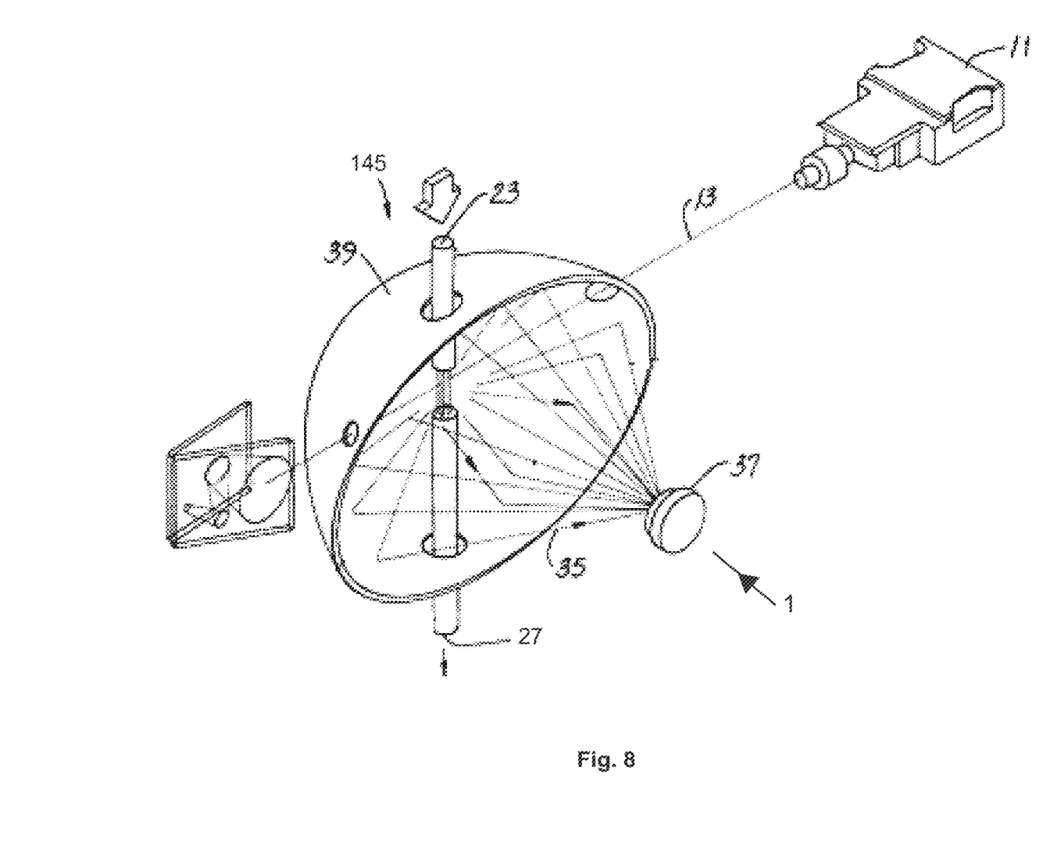
FIG. 8 is a representation of exemplary optomechanical components of the the particle counter of FIG. 1.

FIG. 8 provides one exemplary particle count sensor 145. The sensor 145 includes of a light source (preferably a laser diode type) with beam focusing optics 11 forming a beam of light 13. The system includes an inlet 23 through which fluid from the environment is drawn and an outlet 27. The intersection of the beam and the fluid forms a view volume. Particles entrained in the fluid reflect rays of light 35 into the collection optics 39. The light is reflected or refracted at angles depending on the size and refractive index of the particle. The collection optic (an ellipsoidal mirror in this example) is designed to reflect that light onto a photodetector 37.

The number of photons that intercept the photodetector is a function of the size of the particle intercepting the beam of light. The photons are converted to a current by the photodetector. A cosmic ray 1 can also intercept the detector. Cosmic rays with sufficient energy can influence the photodetector to generate a current that exceeds that of the smallest particle in the sensitivity range of the system.

Figure 9:
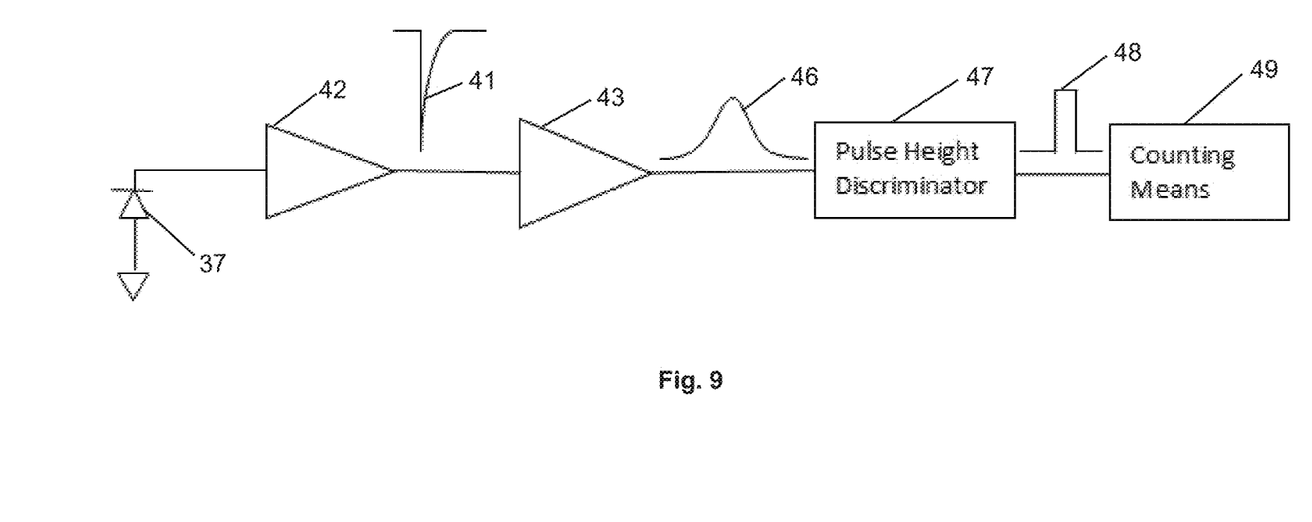
FIG. 9 is a block diagram representing a portion of a particle counting system of the particle counter of FIG. 1.

FIG. 9 is a block diagram of a particle counting system. The current generated by the photodetector 37 is converted to a voltage 41 by a charge sensitive amplifier 42. The charge sensitive amplifier 42 converts the current to the voltage 41 that is a function of a value of a capacitor in a feedback loop. The charge sensitive amplifier 42 can be used in particle counting systems due to its ability to integrate the photodiode current over the entire occupancy time of the particle in the beam, producing an output voltage representative of the total number of photons intercepting the photodetector. A charge sensitive amplifier in a particle counting system is more sensitive to low levels of photons scattered by particles and radiation from cosmic rays.

The particle counting system includes signal processor circuitry 43 which typically consists of a bandpass filter with a center frequency being a function of the occupancy time of the particle in the beam. The bandwidth is chosen to reduce the noise inherent in the detector circuitry and provide a voltage pulse 46 which is overdamped so that the signal recovers to the baseline with no overshoot.

The output of the signal processing circuitry 43 is a voltage pulse 46 having an amplitude that is a function of the particle size. This signal 46 is fed into a pulse height discriminator 47. The pulse height discriminator 47 may utilize a digital signal processor capable of discriminating a plurality of pulse heights and binning them according to corresponding particle sizes or a single voltage comparator capable of discriminating pulses having amplitudes greater than a single threshold. The counting means 49 accumulates the counts 48 representing the particles detected during a time of interest and those counts are used for the measurement purposes of the system.

Figure 10:
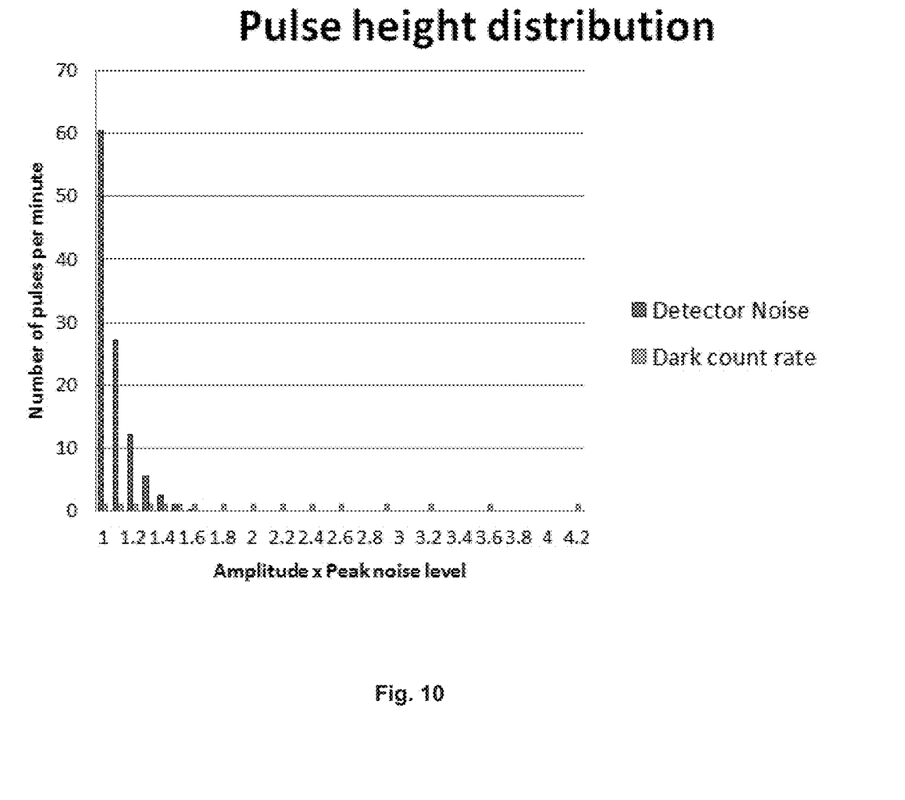
FIG. 10 is a graph of dark count rate compared to detector noise.

The probability of a cosmic ray causing a pulse that is greater than that of a particle in the sensitivity range of the particle counter is a function of the area of the photodetector, the gain of the charge sensitive amplifier and the signal processing circuitry, and the voltage threshold of the peak particle signal for the smallest detectible size of particle. A typical example of the rate of cosmic ray counts and the electronic noise of the detector is shown in FIG. 10. The particle threshold is typically set greater than 1.5 times the peak noise level. The pulses caused by cosmic rays can occur several times a minute above the particle voltage threshold, while the pulses caused by electrical noise much fewer than once every five minutes.

Referring again to FIGS. 3 through 6, environmental sensors, like the particle counter 10, may use centrifugal blowers or regenerative blowers. These types of blowers commonly include a brushless DC (BLDC) motor. A BLDC motor includes a rotor on to which an impeller is attached. The rotor includes a permanent magnet. A BLDC motor also includes a stator, which consists of electromagnetic coils that are energized. The energized coils produce a magnetic field that interacts with a magnetic field of the rotor. An electronic control system senses the angular position of the rotor and energizes the electromagnetic coils in the proper phase relative to the rotor to make it rotate.

In alternative, the example blower 160 shown in the particle counter 10 is a model TF037 micro blower available from Copal Electronics. The blower 160, and more specifically the motor, includes a non-contact fluid dynamic bearing. The non-contact fluid dynamic bearing may also be referred to as an air bearing, hydrodynamic bearing, or aero-dynamic bearing. The air enters the impeller along the rotating axis through a blower intake port 240 and exits through a blower exhaust port 245.

The flow connect block 150 provides a means for connecting the blower vent port 250 from the blower 160 to a channel in the discharge path from the particle count sensor 145. Thus, the gaseous fluid used for venting the motor is not discharged to ambient air. In other words, the blower 160 is sealed to prevent leakage that would introduce errors in the flow communication.

The filter 165 filters particles in the gaseous fluid. The types of particles being filtered depend on the type and design of the filter 165. The filter includes a filter intake port 340 and a filter exhaust port 345. As already discussed, the location of the filter 165 in the flow path can be different from what is shown in the figures. The flow shunt 170, discussed earlier, includes a shunt intake port 350 and a shunt exhaust port 355.

Figure 3:
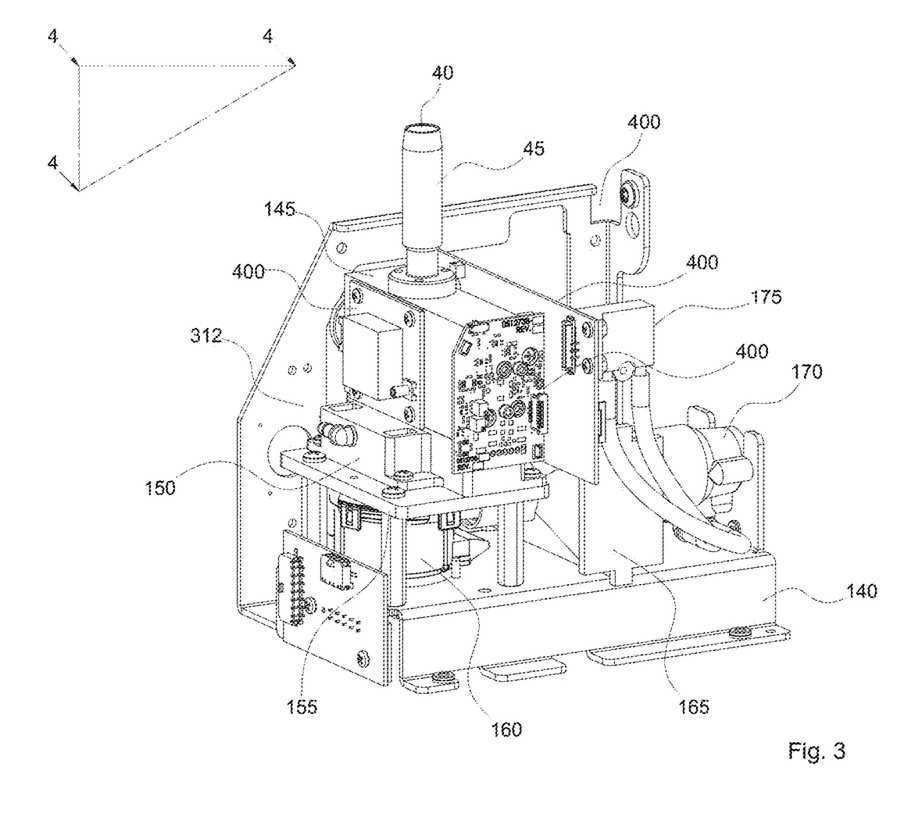
FIG. 3 is a perspective view of an internal portion of the particle counter of FIG. 1 from a third vantage point.
Figure 4:
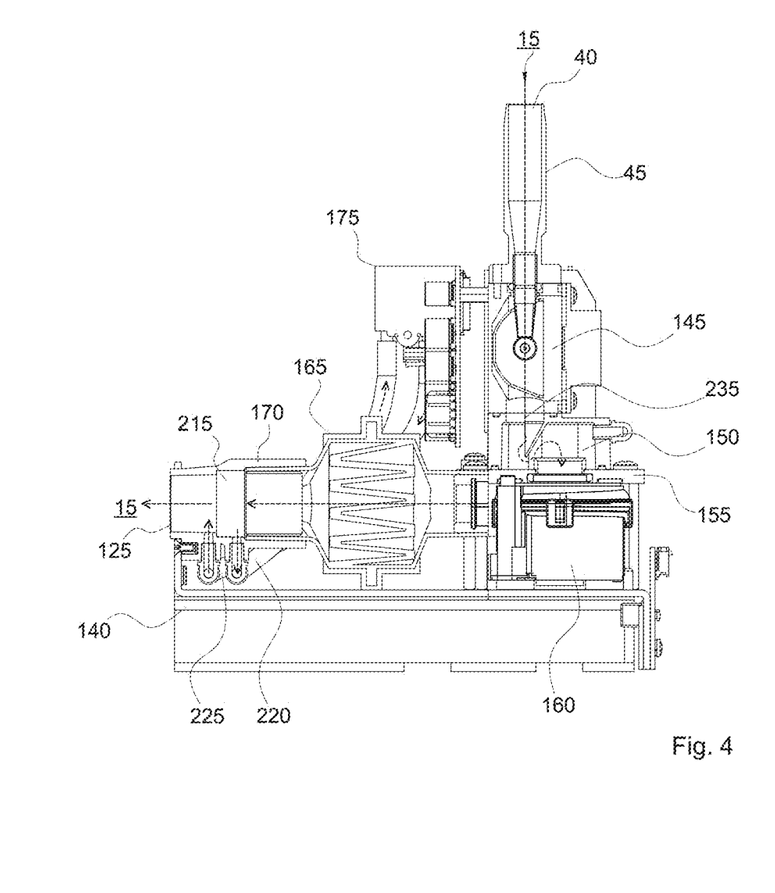
FIG. 4 is a sectional view of an internal portion of the particle counter of FIG. 1 along plane 4-4-4 in FIG. 3.
Figure 5:
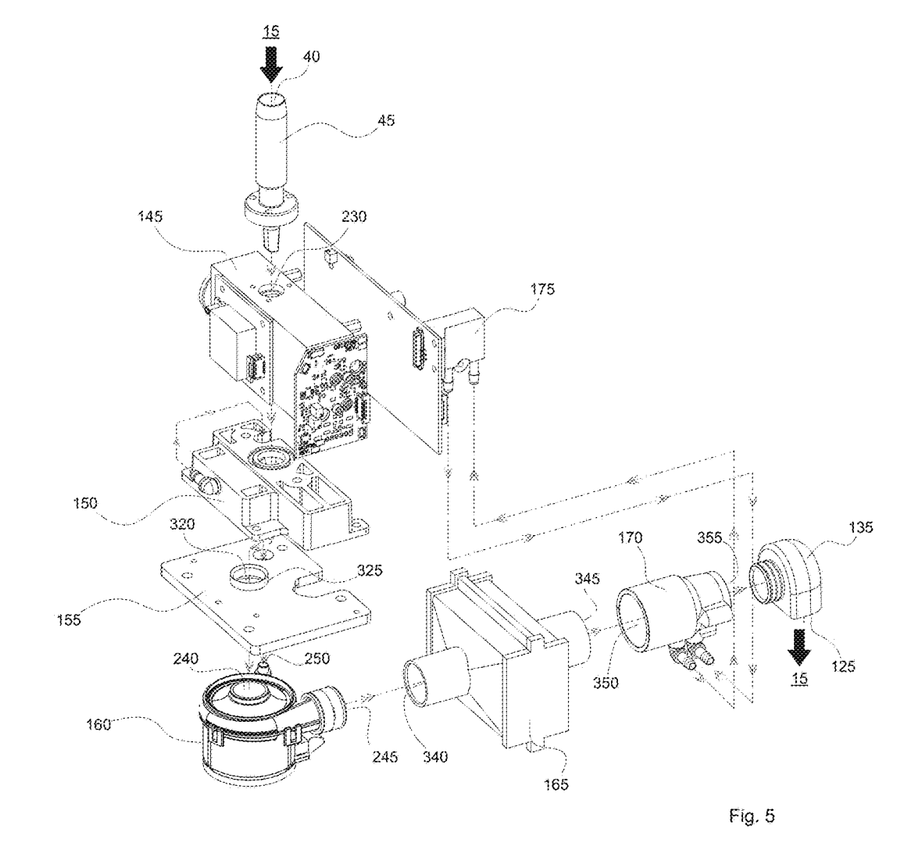
FIG. 5 is an exploded view of a portion of the gaseous-fluid flow system and fluid-flow path through the particle counter of FIG. 1.
Figure 6:
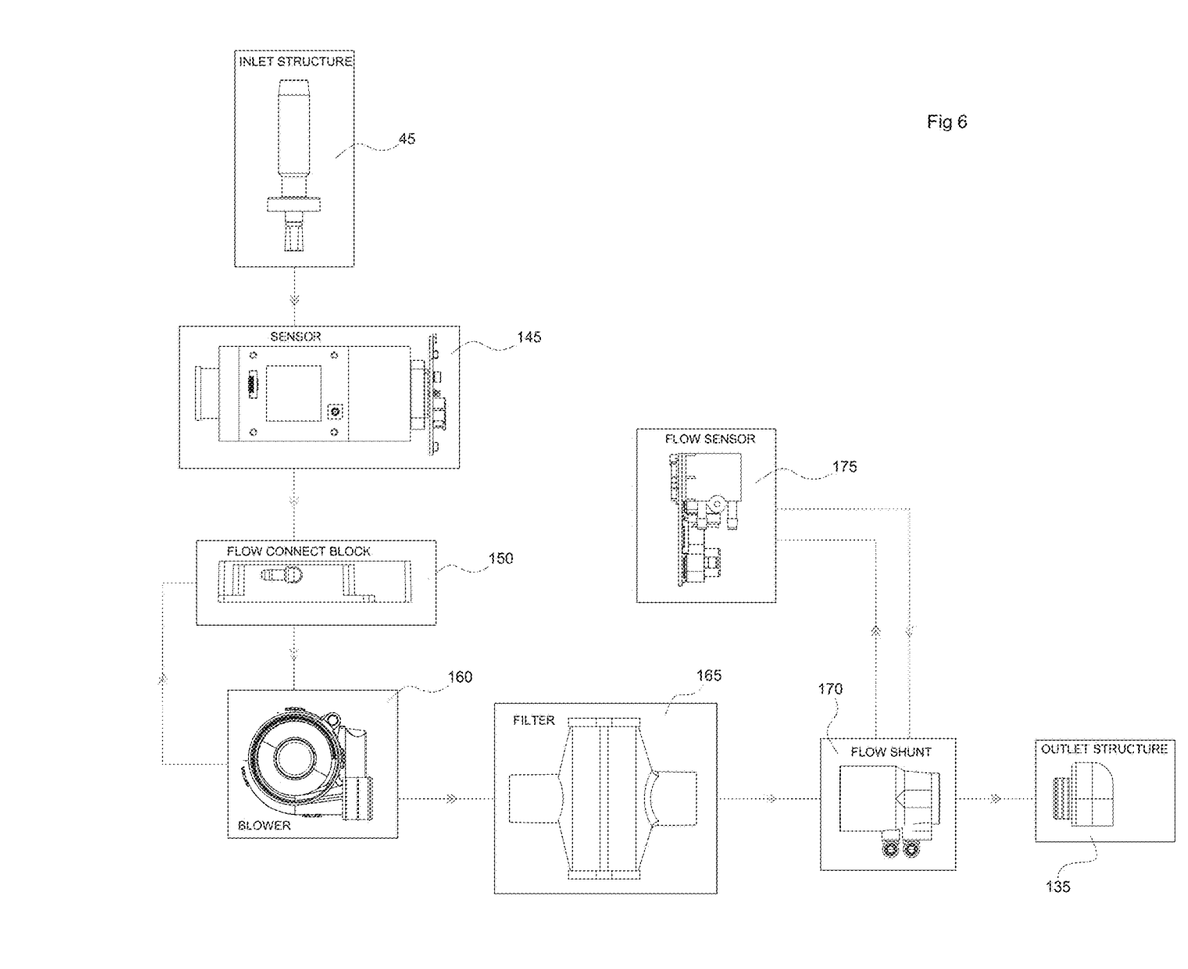
FIG. 6 is a block diagram representing a portion of the gaseous-fluid flow system fluid-flow path of FIG. 5.
Figure 7:
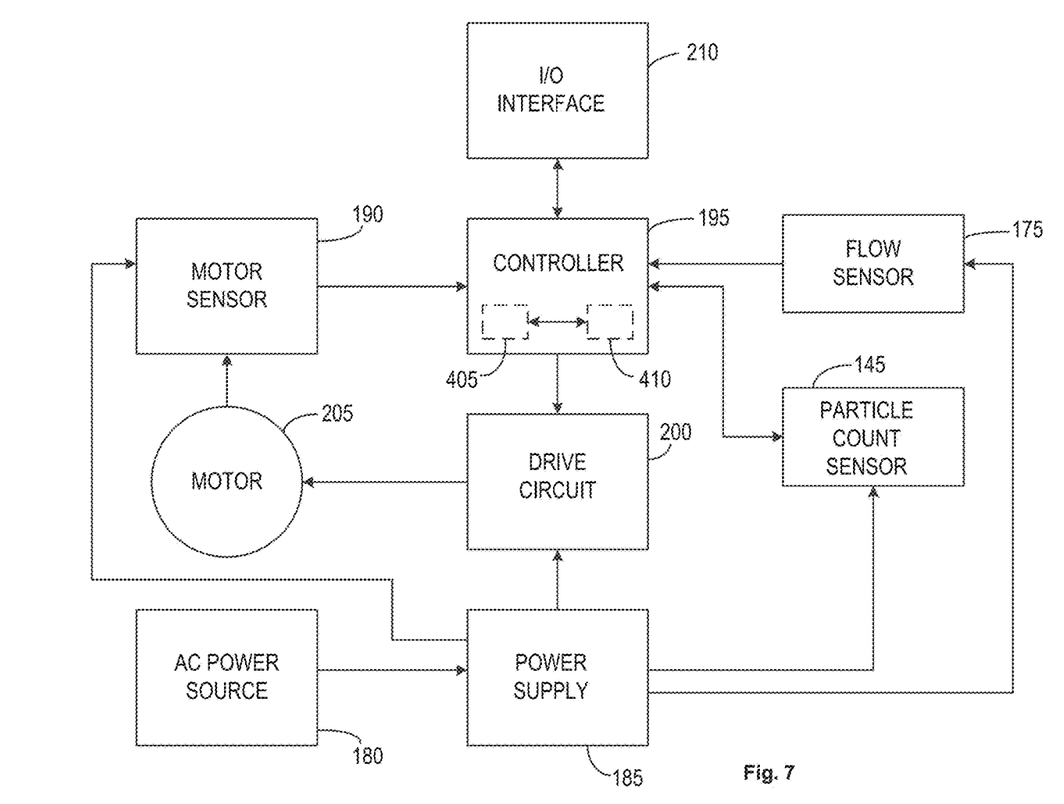
FIG. 7 is a block diagram representing a portion of the control system of the particle counter of FIG. 1.

With reference to FIGS. 3, 5 and 7, the control system further includes multiple circuit boards 400. The circuit boards 400 are populated with a plurality of electrical and electronic components that provide power, operational control, and protection to the particle counter 10. The circuit boards 400 can support control elements (e.g., power supply 185, controller 195, communication input/output (I/O) interface 210, drive circuit 200, etc.) of the particle counter 10 or be coupled to control elements (e.g., motor 205, motor sensor 190, particle count sensor 145, flow sensor 175) of the particle counter 10. The circuit boards also include a plurality of additional passive and active components such as resistors, capacitors, inductors, integrated circuits, and amplifiers. These components are arranged and connected to provide a plurality of electrical functions to the circuit boards including, among other things, filtering, signal conditioning, or voltage regulation.

In some constructions, the controller 195 includes a processor 405 (e.g., a microprocessor, a digital signal processor, a microcontroller, or another suitable programmable device), a memory 410, and a bus. The bus connects various components of the PCB including the memory 410 to the processor 405. The memory 410 includes, for example, a read-only memory ("ROM"), a random access memory ("RAM"), a direct memory access (DMA) an electrically erasable programmable read-only memory ("EEPROM"), a flash memory, a hard disk, or another suitable magnetic, optical, physical, or electronic memory device. The processor 405 is connected to the memory 410 and executes firmware that is capable of being stored in the RAM (e.g., during execution), the ROM (e.g., on a generally permanent basis), or another non-transitory computer readable medium such as another memory or a disc. Additionally or alternatively, the memory 410 is included in the processor 405. It is also envisioned that the processor 405 can encompass multiple processors and the memory 410 can encompass multiple memories. The controller 195 also includes an input/output system for transferring data with other components (e.g., the communication I/O 210), receiving sensory signals (analog and/or digital) from other components (e.g., the motor sensor 190, the flow sensor 175, and the particle count sensor 145), and output control signals to other components (e.g., drive circuit 200). It is to be understood that the control system may be operable to perform other functions and operations not described herein.

In some constructions of the particle counter 10, the flow sensor 175 is a mass-flow sensor. Alternatively, a differential pressure transducer can be coupled to determine a parameter of the flow. A controller of the flow sensor 175 is operable to determine a parameter of the gaseous fluid and/or the gaseous-fluid flow through the particle counter 10 (e.g. mass, volume, speed, composition, etc.) based on information generated by the mass-flow sensor, the differential pressure transducer, or other input devices not specifically discussed herein.

In one example, the flow sensor 175 generates a signal indicative of the mass of gaseous fluid flowing through the particle counter 10 over a predetermined period of time. The signal generated by the flow sensor 175 can be supplied to the controller 195 to control the operation of the blower 160 and adjust the gaseous-fluid flow to a desired amount. In this particular example, it may be desired to maintain the gaseous-fluid flow at 100 liters per minute (LPM). The flow sensor 175 is operable to detect a variation of the gaseous-fluid flow to control the operation of the blower assembly and adjust the gaseous-fluid flow to 100 LPM. It is to be understood that this flow rate is only one example. Moreover, it is possible to operate the blower 160 to generate a variable flow rate over time through the particle counter 10 based on other information (e.g., temperature, humidity, particle count). It is envisioned that the sensor controller can be combined with the controller 195 such that the raw signal from the flow sensor 175 is provided to the controller 195.

The particle counter 10 can communicate with other devices via a wired or wireless connection through the communications I/O interface 210. The wireless communication can be via a wireless access point. The term "wired" is intended to define means of connection such as USB cable, DSL cable, Ethernet cable, and others. Similarly, the communication with the device can be over a network.

The power supply 185 supplies nominal voltages to the electrical and electronic components of the control system. The power supply 185 can be powered by mains power having nominal line voltages or a DC power source 180 (e.g., a battery). In one construction the power source 180 provides between 12 VDC and 24 VDC.

As discussed, the control system includes the controller 195, the drive circuit 200, the motor sensor 190, and the motor 205. Generally speaking, the controller 195 drives the motor 205 using the drive circuit 200 and based on sensed parameters. One example sensed parameter is rotor positioning determined through the motor sensor 190. Another parameter is the gaseous fluid flow through the particle counter 10. Further exemplary operations are discussed below.

In one operation, the particle counter 10 moves a measured and controlled volume of fluid through the particle counter sensor 145. Particles being detected are entrained in the fluid. The sensor 145 includes a light source directed in a beam (e.g., a laser beam) and an inlet that directs the flow of fluid through the beam of light. Particles entrained in the fluid scatter light on to an optical collection system, which directs the scattered light to intercept a photodetector. The particle count sensor 145 includes circuitry connected to the photodetector for converting scattered light to electrical signals. The controller 195 is operable to determine information regarding the particles (e.g., particle size, velocity, composition) based on the voltage pulse generated by the particle count sensor 145. The information determined by the controller 195 can be saved in memory.

The photodetector and signal processing system (e.g., the particle count sensor 145) produce an electrical pulse when a particle passes through the beam of light and scatters photons that intercept the photodetector. The photodetector and signal processing system is also designed to be sensitive to detect cosmic rays so that when a cosmic ray with sufficient energy intercepts the photo diode, an electrical pulse is produced that is undistinguishable from a particle pulse. The particle detection system includes a particle counter that increments when the pulse produced by the signal processing system exceeds an amplitude that corresponds to a given particle size. The pulse can be the result of a particle or a cosmic ray.

The counting system can also include a dark counter that increments at a rate that is a function of the average rate of the counts that occur from cosmic rays. When the detection system produces a pulse, the counting system evaluates the dark counter. If the dark counter is not zero, it decrements the dark counter and does not increment the particle counter. If the cosmic ray counter is zero, the system increments the particle counter, which represents the particle count with dark counts removed. This particle counter is used for reporting the particle count to users of the system.

Figure 11:
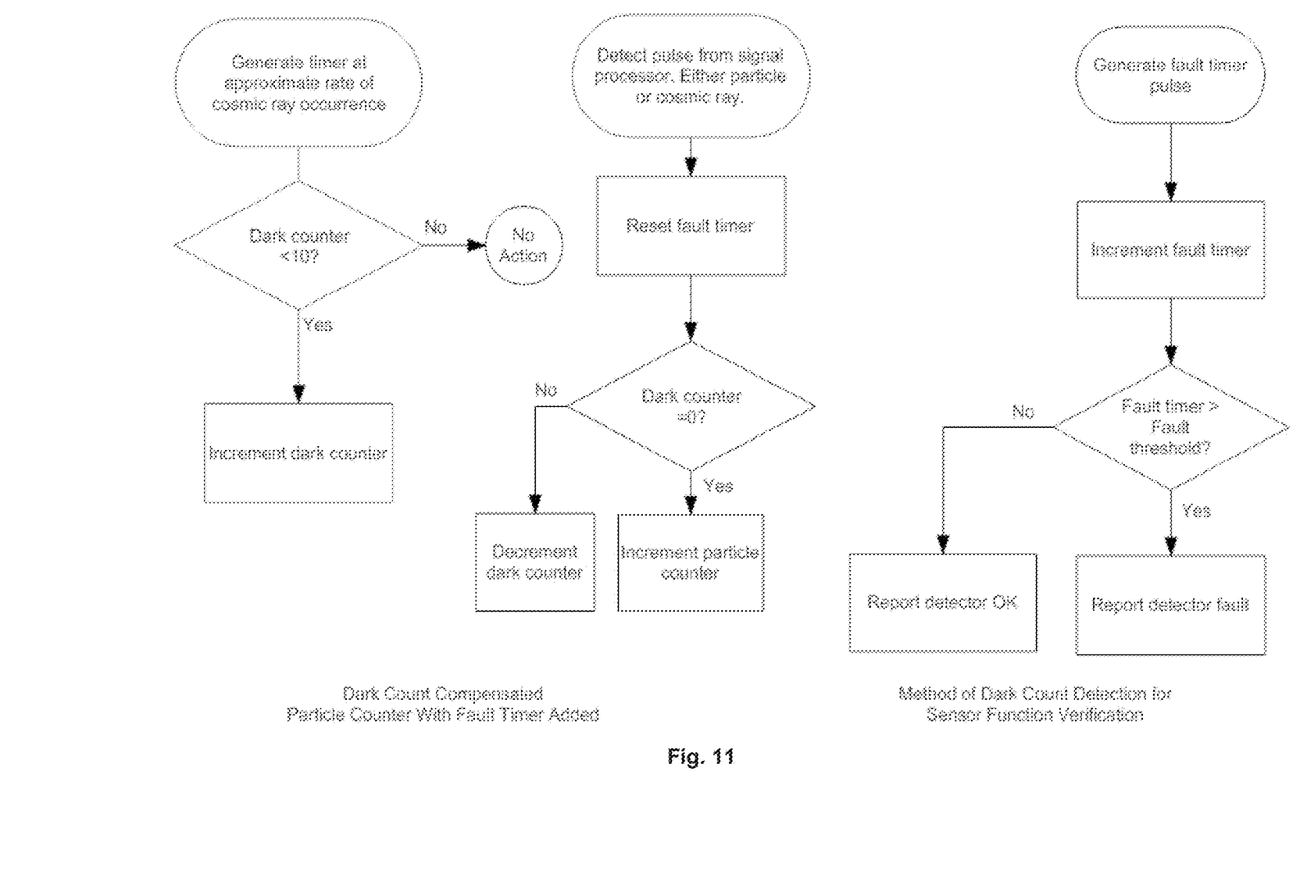
FIG. 11 is flow charts of a method of dark count compensation and sensor verification.

In an improved operation, the counting system includes an additional means to test the number of particle counts and the number of dark counts. If the number has not in increased for a time sufficient for at least one dark count to have occurred, the system will report a failure of the particle counter. FIG. 11 provides an exemplary implementation of this improved operation.

Accordingly, the invention provides a new and useful environmental sensor and method of operating the same. Various features and advantages of the invention are set forth in the following claims.

What is claimed is:

1. A gaseous-fluid environmental sensor, comprising:
 a gaseous-fluid flow system defining a flow path coupling an intake port to an exhaust port,
 a particle count sensor to sense particles in the fluid and a cosmic ray;
 a controller electrically coupled to the particle count sensor, the controller being configured to
  store a dark count,
  store a compensated particle count based on the signal from the particle count sensor and the dark count, and
  determine whether the particle count sensor has a fault based on the particle count sensor not sensing a particle or a cosmic ray in a time period.

2. The sensor of claim 1, wherein the particle count sensor is configured to provide a pulse when a particle is within a size range.

3. The sensor of claim 1, wherein the particle count sensor includes an aerosol particle sensor.

4. The sensor of claim 1, and further comprising a display coupled to the controller, the display for displaying the particle count.

5. The sensor of claim 1, wherein the gaseous-fluid flow system includes a blower and a flow sensor, the blower including a motor and the flow sensor sensing a flow-related parameter.

6. The sensor of claim 5, wherein the controller is further configured to generate an error signal when the fault is present, wherein the controller is further configured to stop the blower based on the error signal.

7. The sensor of claim 1, wherein the controller is further configured to generate an error signal when the fault is present, and report the fault in stored data records.

8. The sensor of claim 1, wherein the controller is further configured to generate an error signal when the fault is present, and annunciating the fault on visual indicators.

9. The sensor of claim 1, wherein the controller is further configured to
 increment the stored dark count,
 detect a pulse based on the particle count sensor sensing a particle or a cosmic ray,
 decrement the stored dark count when the stored dark count is not zero and in response to the detected pulse, and
 increment the stored compensated particle count when the stored dark count is zero and in response to the detected pulse.

10. The sensor of claim 9, wherein the controller is further configured to increment the stored dark count based on a periodic time interval.

11. A method of controlling a gaseous-fluid environmental sensor having a particle count sensor, the method comprising:
 creating a flow of fluid from a space through the gaseous-fluid environmental sensor;
 sensing particles in the fluid with the particle count sensor;
 sensing cosmic rays with the particle count sensor;
 storing a dark count;
 storing a compensated particle count based on the sensed particles, the sensed cosmic rays, and the stored dark count;
 determining whether the particle count sensor has a fault based on the particle count sensor not sensing a particle or a cosmic ray in a time period.

12. The method of claim 11, and further comprising generating a pulse when a particle is within a size range.

13. The method of claim 11, and further comprising generating an error signal when the fault is present, and stopping the flow of fluid based on the error signal.

14. The method of claim 11, and further comprising generating an error signal when the fault is present, and reporting the fault in stored data records.

15. The method of claim 11, and further comprising generating an error signal when the fault is present, and annunciating the fault on visual indicators.

16. The method of claim 11, and further comprising incrementing the stored dark count, detecting a pulse based on the particle count sensor sensing a particle or a cosmic ray, decrementing the stored dark count when the stored dark count is not zero and in response to the detected pulse, and incrementing the stored compensated particle count when the stored dark count is zero and in response to the detected pulse.

17. The method of claim 16, wherein the incrementing the stored dark count includes incrementing the stored dark count based on a periodic time interval.

* * * * *